(12) United States Patent
Baskerville et al.

(10) Patent No.: US 10,413,809 B2
(45) Date of Patent: Sep. 17, 2019

(54) PORTABLE SYSTEM AND METHOD FOR IDENTIFYING ROULETTE WHEEL BIASES

(71) Applicants: Paul Baskerville, Staffordshire (GB); Shannon Nipp, Las Vegas, NV (US)

(72) Inventors: Paul Baskerville, Staffordshire (GB); Shannon Nipp, Las Vegas, NV (US)

(73) Assignee: TCS John Huxley Europe Ltd., Staffordshire (GB)

( * ) Notice: Subject to any disclaimer, the term of this patent is extended or adjusted under 35 U.S.C. 154(b) by 213 days.

(21) Appl. No.: 15/480,272

(22) Filed: Apr. 5, 2017

(65) Prior Publication Data
US 2018/0290049 A1 Oct. 11, 2018

(51) Int. Cl.
| | | |
|---|---|---|
| *A63F 5/00* | (2006.01) | |
| *A63F 11/00* | (2006.01) | |
| *G01N 3/303* | (2006.01) | |
| *G01N 29/04* | (2006.01) | |
| *G01N 29/48* | (2006.01) | |
| *A63F 9/24* | (2006.01) | |

(52) U.S. Cl.
CPC .............. *A63F 5/00* (2013.01); *A63F 11/00* (2013.01); *G01N 3/303* (2013.01); *G01N 29/045* (2013.01); *G01N 29/48* (2013.01); *A63F 2009/2445* (2013.01); *A63F 2250/10* (2013.01)

(58) Field of Classification Search
None
See application file for complete search history.

(56) References Cited

U.S. PATENT DOCUMENTS

| | | | | |
|---|---|---|---|---|
| 5,836,583 | A * | 11/1998 | Towers | A63F 5/00 |
| | | | | 273/142 B |
| 8,028,993 | B2 * | 10/2011 | Witty | A63F 5/00 |
| | | | | 273/142 E |
| 8,221,214 | B2 * | 7/2012 | Nicely | G07F 17/32 |
| | | | | 463/20 |
| 8,767,215 | B2 * | 7/2014 | Cantin | G01V 8/12 |
| | | | | 356/445 |
| 9,717,980 | B2 * | 8/2017 | Pearce | A63F 5/00 |
| 10,118,087 | B2 * | 11/2018 | Mercer | A63F 5/0005 |

* cited by examiner

*Primary Examiner* — Peter J Macchiarolo
*Assistant Examiner* — Jermaine L Jenkins
(74) *Attorney, Agent, or Firm* — FisherBroyles, LLP; Rob L. Phillips (57) ABSTRACT

A portable system and method for identifying roulette wheel biases includes a frame member rotatably attachable to a roulette wheel proximate a turret support, a ball-drop tube slidably engaged to the frame member and a laser positioned to measure at least a bounce height of a roulette ball dropped through the ball-drop tube onto selective areas of the roulette wheel. One or more sensors may be positioned to trigger the laser responsive to a roulette ball being dropped through said ball-drop tube. Software analyzes the bounce height to determine dead spots and hot spots on the roulette wheel. Sound waves may also be measured to determine dead spots and hot spots.

16 Claims, 13 Drawing Sheets

PORTABLE SYSTEM AND METHOD FOR IDENTIFYING ROULETTE WHEEL BIASES

FIELD OF THE INVENTION

The embodiments of the present invention relate to a portable system for identifying biases in the number ring, separator ring, cone and lower ball track of a roulette wheel.

BACKGROUND

Roulette wheels have been used for decades to generate truly random outcomes. Unfortunately, roulette wheels can develop biases over time. Such biases or dead areas can influence which pocket in which the roulette ball lands thereby defeating the truly random nature of the roulette wheel.

Accordingly, it would be beneficial to develop a system and method for identifying any roulette wheel biases. Advantageously, the system should be portable.

SUMMARY

A first embodiment of the present invention involves a system comprising: a frame member rotatably attachable to a roulette wheel proximate a turret support; a ball-drop tube slidably engaged to said frame member, said ball-drop tube slidable from near a center of said roulette wheel to an outer section of said roulette wheel; and a laser positioned to measure at least a bounce height of a roulette ball dropped through said ball-drop tube onto one or more of the following: a cone, separator ring, number ring and lower ball track of said roulette wheel. In another embodiment, one or more sensors are positioned to trigger said laser responsive to a roulette ball being dropped through said ball-drop tube.

The bounce height and related data associated with the roulette ball drop is automatically transmitted to a software module or application which stores said bounce height and related data and provides a user with a visual presentation of the same. In one embodiment, a standard deviation protocol is used to determine whether any ball-drop data reflects a roulette wheel bias.

A method of identifying roulette wheel biases comprises: (i) rotatably attaching to a roulette wheel a device comprising a frame member, ball-drop tube connected to said frame member, and at least a laser configured to measure a roulette ball bounce height; (ii) positioning said frame member and ball-drop tube such that said ball-drop tube is above a cone area, number ring, separator ring or lower ball track of said roulette wheel; (iii) dropping a roulette ball into said ball tube; (iv) recording at least a bounce height associated with said ball drop; (v) repeating steps (ii)-(iv) as necessary; and (v) evaluating said at least bounce height associated with all ball drops to determine roulette wheel biases.

Other variations, embodiments and features of the present invention will become evident from the following detailed description, drawings and claims.

DETAILED DESCRIPTION

For the purposes of promoting an understanding of the principles in accordance with the embodiments of the present invention, reference will now be made to the embodiments illustrated in the drawings and specific language will be used to describe the same. It will nevertheless be understood that no limitation of the scope of the invention is thereby intended. Any alterations and further modifications of the inventive feature illustrated herein, and any additional applications of the principles of the invention as illustrated herein, which would normally occur to one skilled in the relevant art and having possession of this disclosure, are to be considered within the scope of the invention claimed.

As will be appreciated by one skilled in the art, the embodiments of the present invention combine software and hardware. Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), and optical storage device, a magnetic storage device, or any suitable combination of the foregoing. In the context of this document, a computer readable storage medium may be any tangible medium that can contain or store a program for use by or in connection with an instruction execution system, apparatus, or device.

Computer program code for carrying out operations for embodiments of the present invention may be written in any combination of one or more programming languages, including an object oriented programming language such as Java, Smalltalk, C++ or the like or conventional procedural programming languages, such as the "C" programming language, AJAX, PHP, HTML, XHTML, Ruby, CSS or similar programming languages. The programming code may be configured in an application, an operating system, as part of a system firmware, or any suitable combination thereof.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

Figure 1:
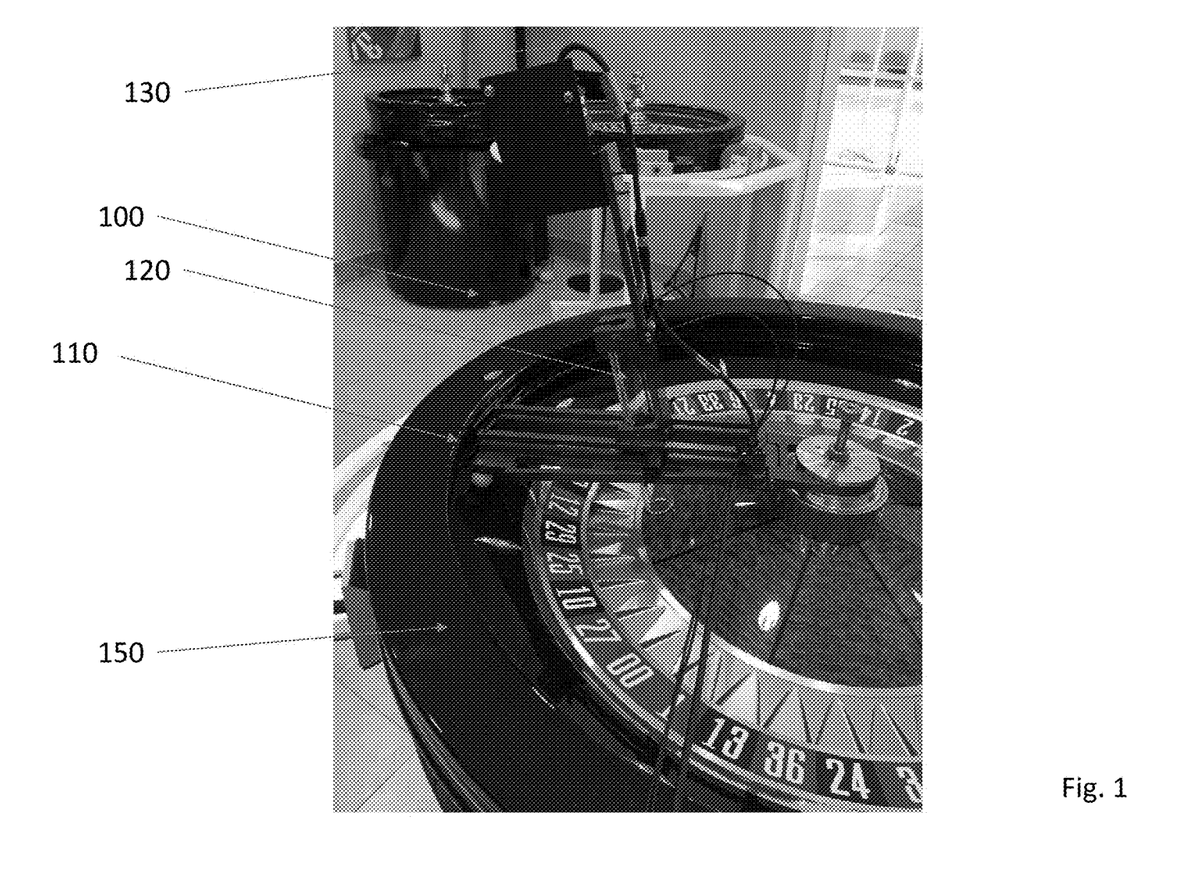
FIGS. 1 and 2 illustrate views of a portable system for identifying roulette wheel biases according to the embodiments of the present invention.
Figure 2:
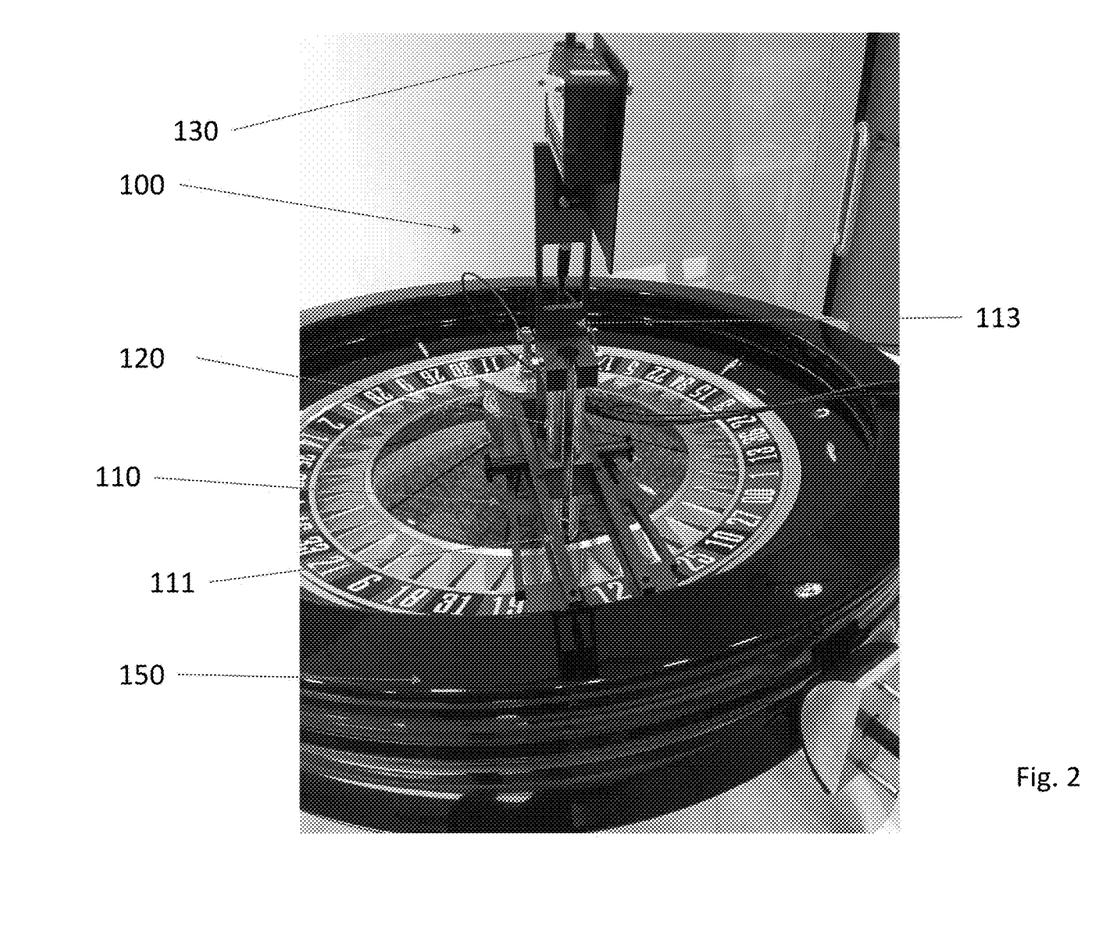

Now referencing FIGS. 1 and 2, in broad terms, a system 100 for identifying roulette biases comprises a frame member 110, a ball-drop tube 120, a laser 130 and optionally one or more sensors 167, 168. The most common roulette wheel bias relates to areas on the roulette wheel which are dead spots or hot spots. The embodiments of the present invention maybe used to identify dead spots and hot spots in the number ring (including the roulette numbers), separator ring (including the ball pockets), cone and lower ball track of a roulette wheel. When the roulette ball makes contacts with dead spots or hot spots, the roulette ball tends to react in an abnormal fashion creating outcomes which are not truly random (e.g., landing in certain ball pockets more often than others). The non-random outcomes may provide players with an advantage over the casino or cause players to question the veracity of the roulette wheel and its operator. The system 100 is configured to detect such dead and overly sensitive areas as detailed below.

Figure 3:
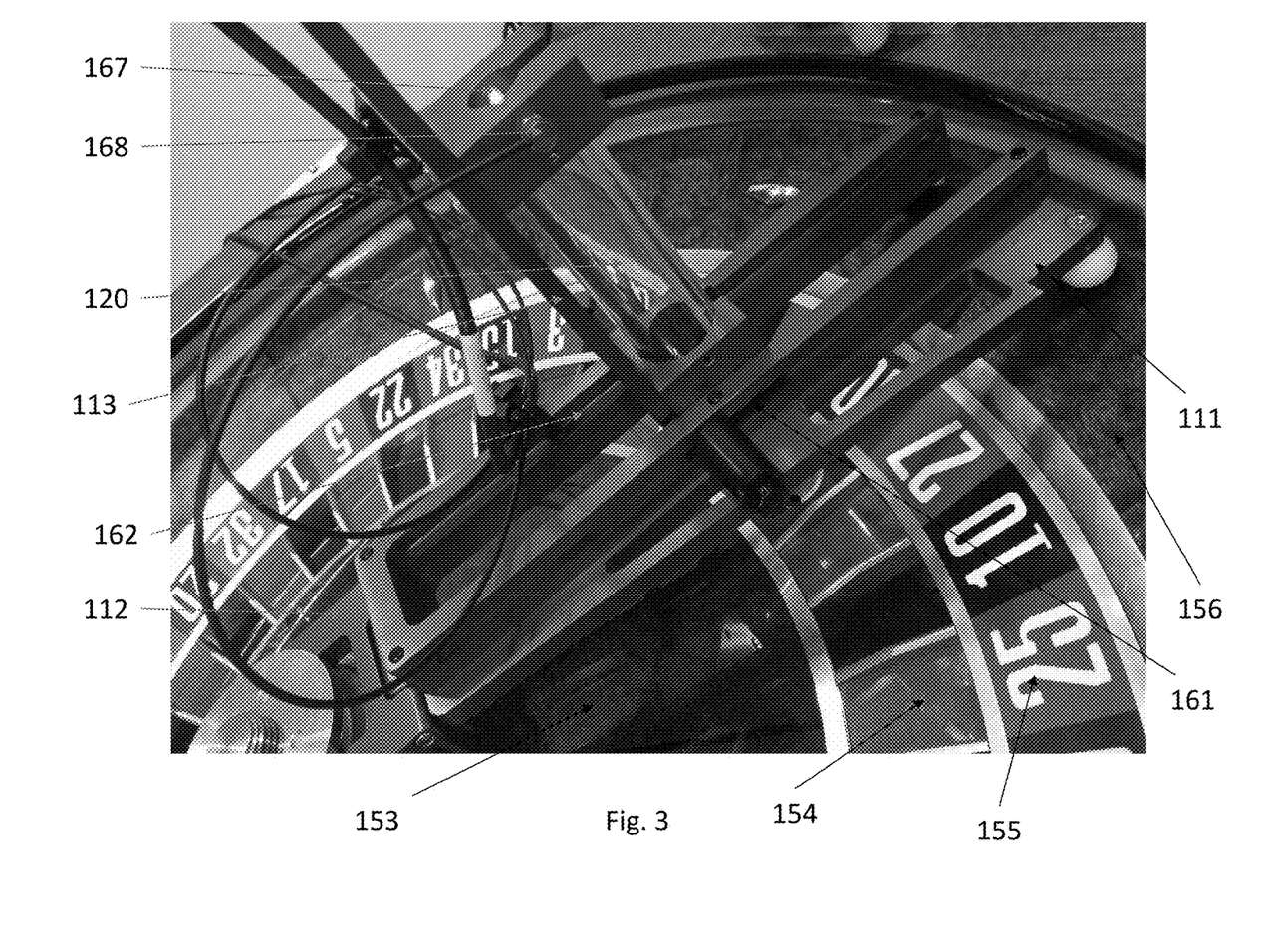
FIG. 3 illustrates a view of a frame member and ball-drop tube according to the embodiments of the present invention.
Figure 7:
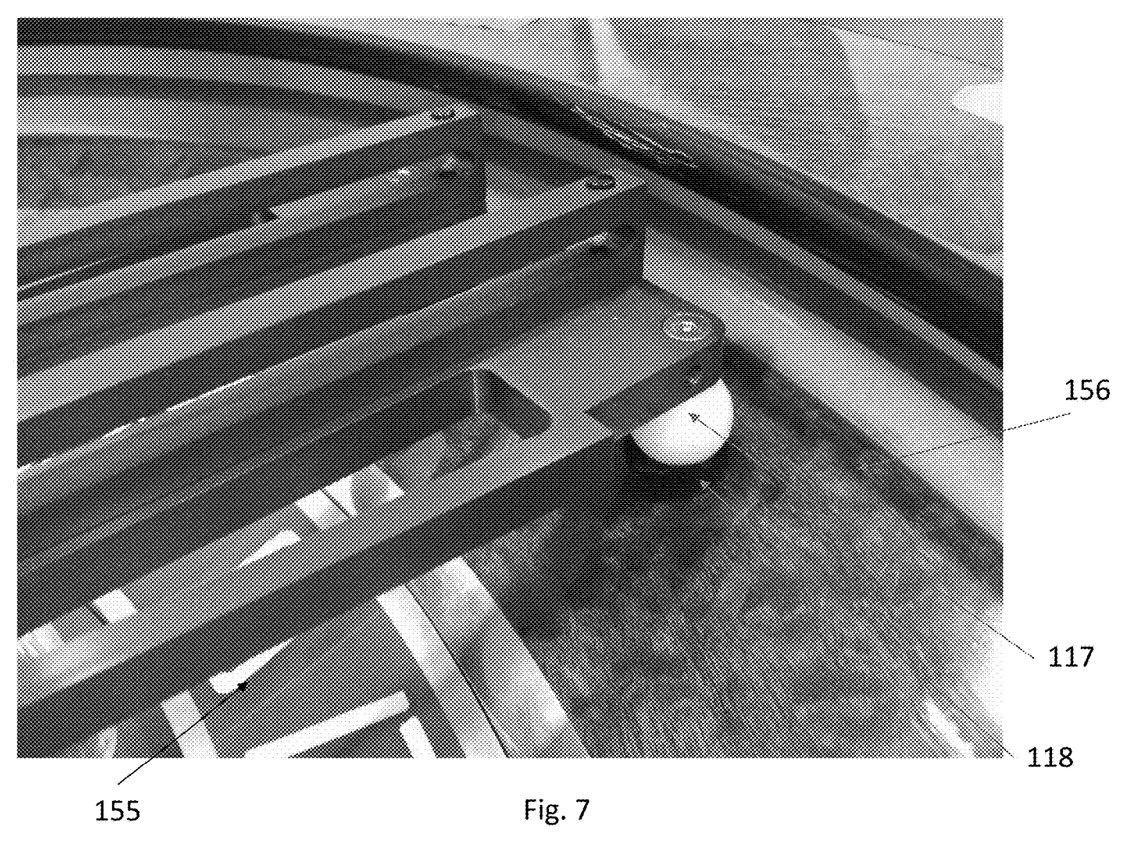
FIG. 7 illustrates an outer portion of the frame member according to the embodiments of the present invention.

As best seen in FIG. 3, one end of the frame member 110 includes a hinged flange 112 configured to receive a threaded connector 114 thereby rotatably joining the frame member 110 to a turret support 152 of a roulette wheel 150. In this manner, the frame member 110 may rotate 360° in a generally horizontal plane around the roulette wheel 150. As shown in FIG. 7, an outer portion of the frame member 110 contacts a separator ring 154 providing a smooth contact for easily rotation of the frame member 110 about the roulette wheel 150 as needed (as shown including a fixed roulette ball 117 and pad 118). The frame member 110 may pivot upward about the hinged flange 112 (see arrow A) permitting a roulette ball dropped into the drop-ball tube 120 to be retrieved.

Figure 4:
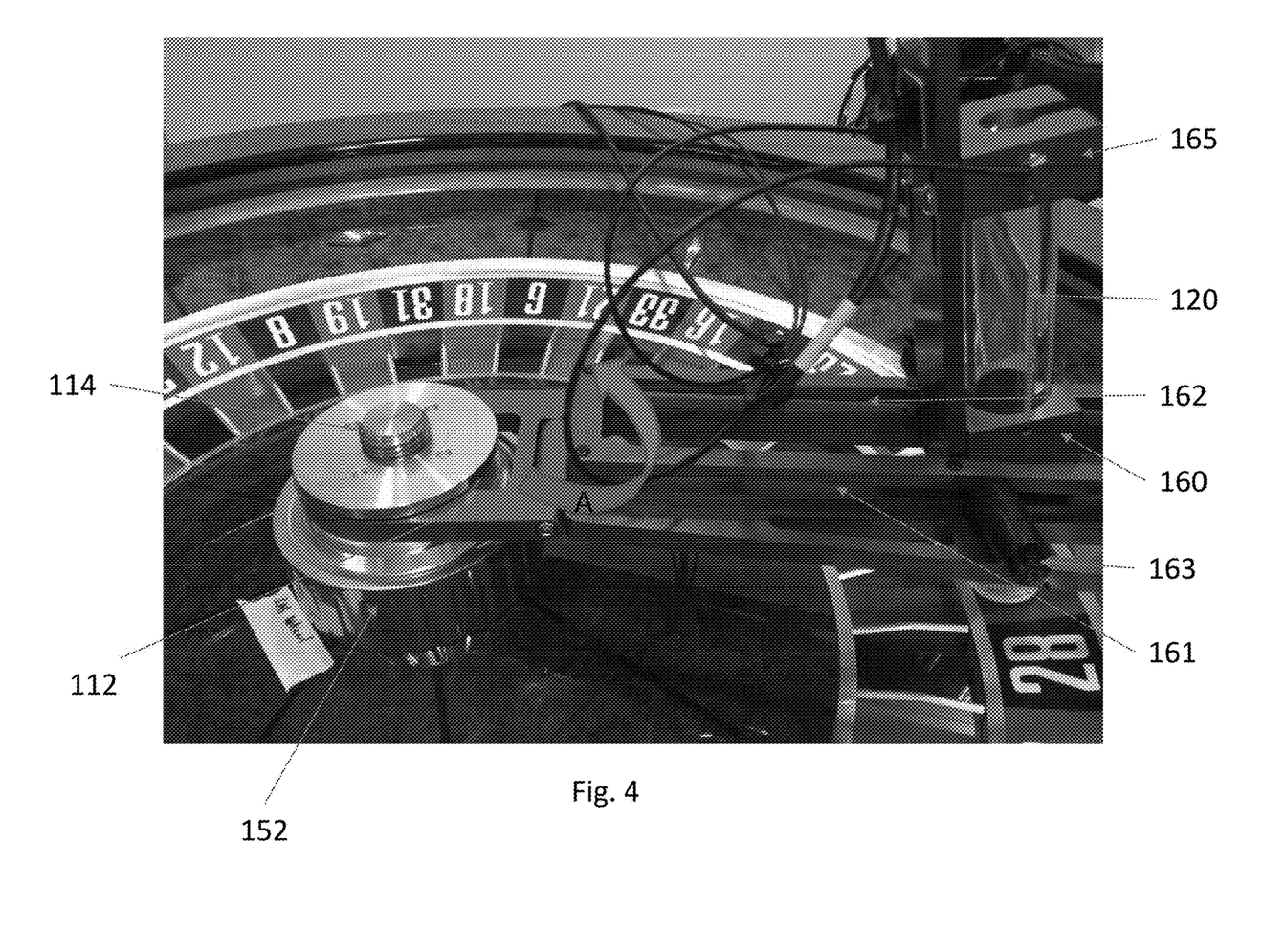
FIG. 4 illustrates a view of the frame member and attachment means according to the embodiments of the present invention.
Figure 5:
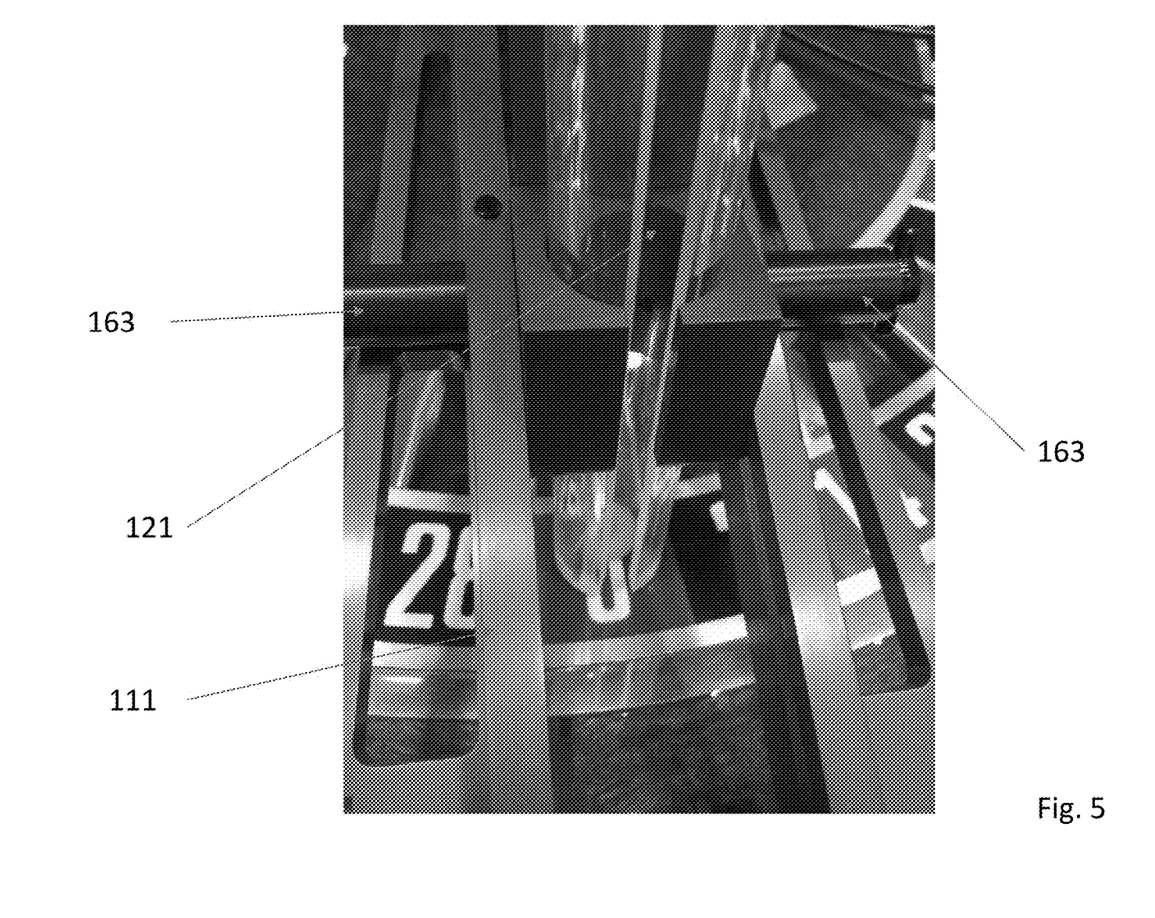
FIG. 5 illustrates a view of a bottom portion of the ball-drop tube according to the embodiments of the present invention.

The frame member 110 is made up of a horizontal unit 111 and vertical unit 113. The horizontal unit 111 being configured to allow the ball-drop tube 120 to slide radially from the cone 153 to the separator ring 154 to the number ring 155 to the lower ball track 156. As shown in FIGS. 3 through 5, a lower block member 160, configured to receive a central portion of the ball-drop tube 120, fits between, and slides along, spaced slots 161, 162 of the horizontal unit 111. Adjustable mounting screws 163 permit the lower block member 160 to be loosened for radially sliding along the spaced slots 161, 162 and tightened when positioned properly. Referencing FIG. 6, an upper block member 165 defines a ball-drop opening 166 proximate a top of the ball-drop tube 120. In one embodiment, the ball-drop opening 166 in the upper block 165 is nominally large in diameter than a roulette ball thereby eliminating any variance with the ball drop. Both the lower block member 160 and upper block member 165 are fixed to the vertical unit 113.

Figure 8:
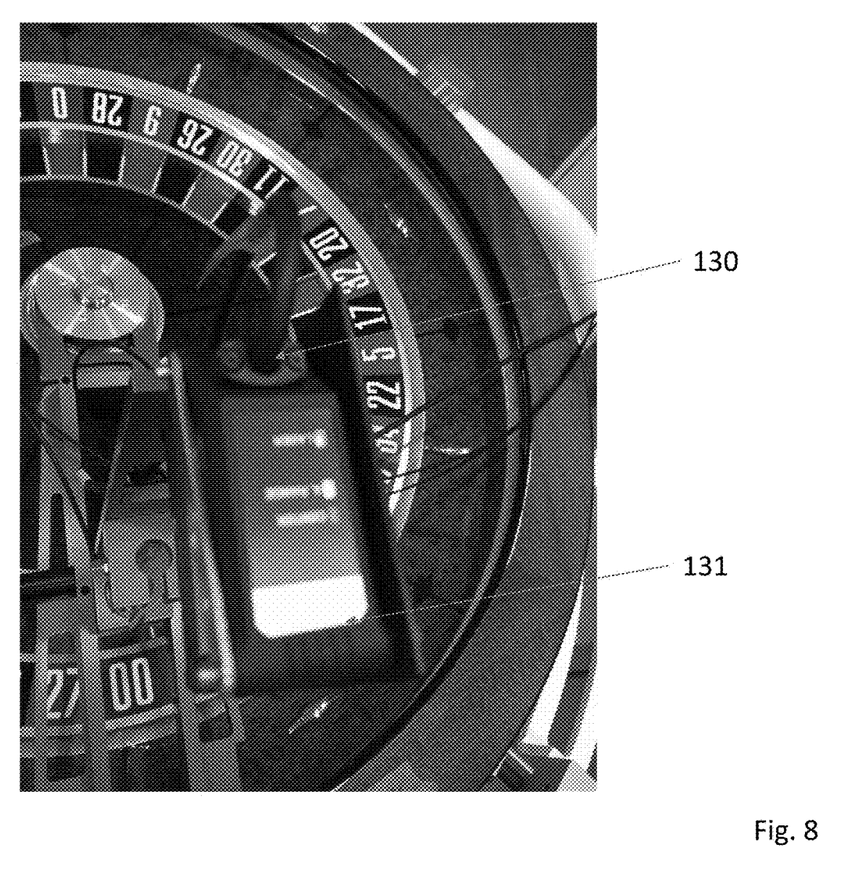
FIG. 8 illustrates an upper view of the portable system for identifying roulette wheel biases according to the embodiments of the present invention.

FIG. 8 shows the laser 130 attached to a top of the vertical unit 113. The laser 130 is positioned to emit light energy (e.g., infrared) downward through the ball-drop tube 120. A cut-out 121 along at least a portion of the ball-drop tube 120 creates a clear view for a laser receiver 131 to receive light energy reflected off of said roulette ball to determine a bounce height associated therewith. In one embodiment, the ball-drop tube 120 is fabricated of clear acrylic.

Figure 6:
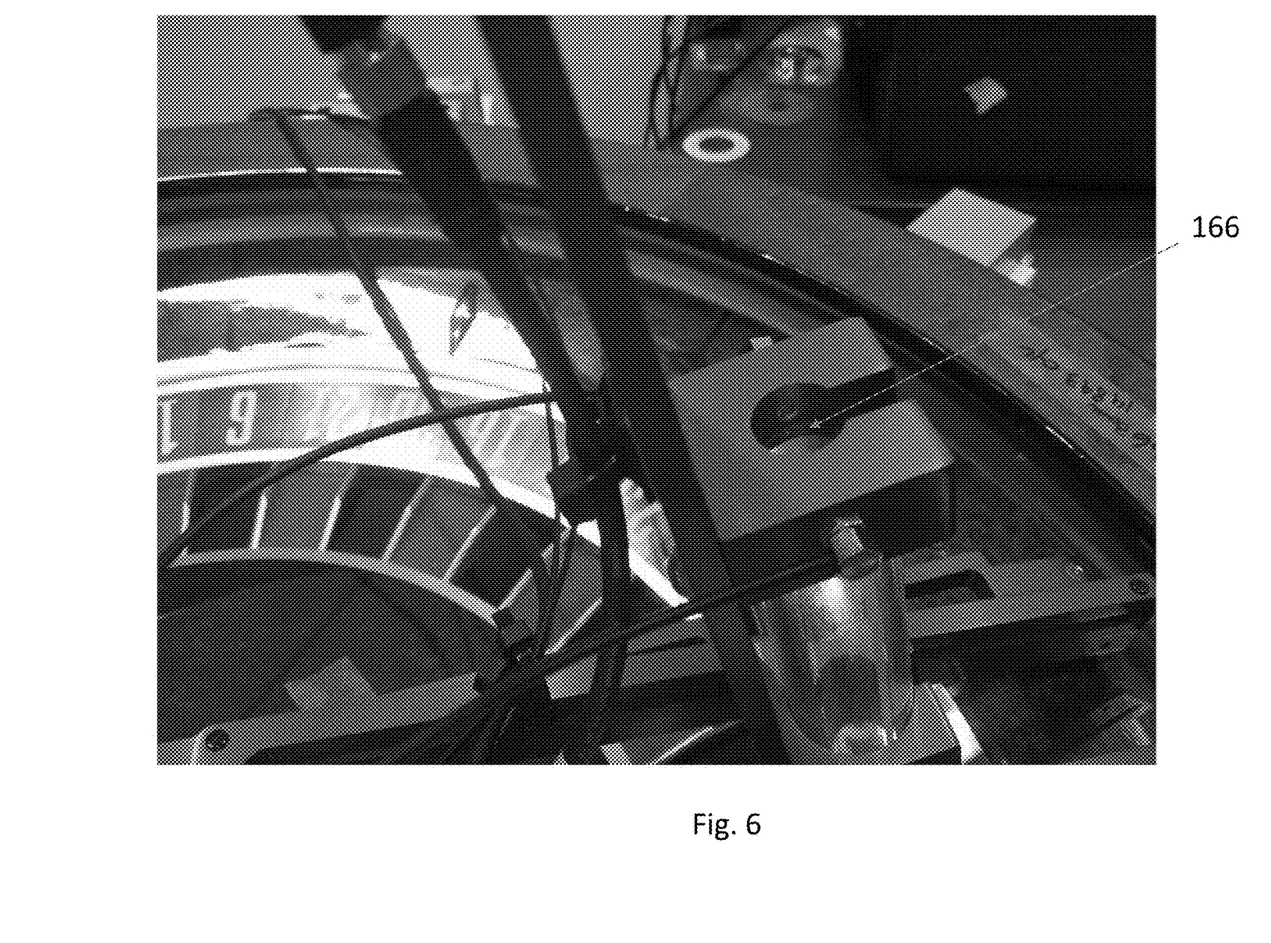
FIG. 6 illustrates an upper view of the ball-drop tube according to the embodiments of the present invention.

The upper block member 165 includes two sensors 167, 168, configured to detect a start of the ball drop cycle. The sensors 167, 168, as shown, are integrated into opposite walls of the upper block 165 and configured to detect insertion and release of the roulette ball. In this manner, when the roulette ball is first inserted into the ball-drop tube 120 via the ball-drop opening, the sensors 167, 168 detect the same. Then, when the roulette ball leaves the space between the sensors 167, 168 (i.e., the sensors 167, 168 detect the roulette ball has been dropped) the laser 130 is triggered to start emitting light energy. This process prevents the laser 130 from generating a bounce height associated with the insertion of the roulette ball into the ball-drop tube 120. Alternatively, sensors may be placed elsewhere along the ball-drop tube 120 below the ball-drop opening 160 which, when interrupted, trigger the laser 130. In one embodiment, the sensors are fiber optic sensors but other types of sensors may be used.

Figure 9A:
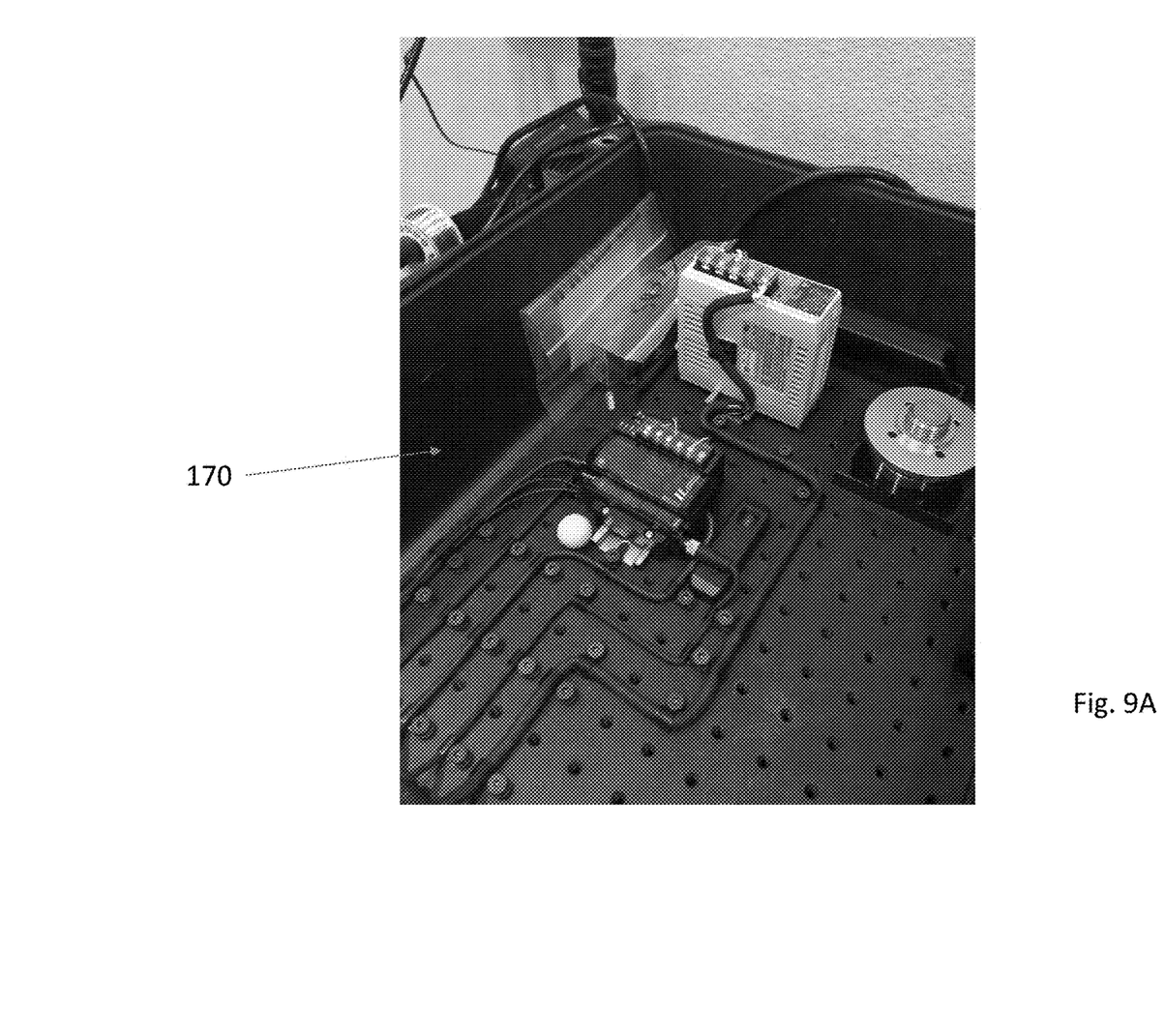
FIGS. 9A and 9B illustrate views a case equipped to carry the system according to the embodiments of the present invention.
Figure 9B:
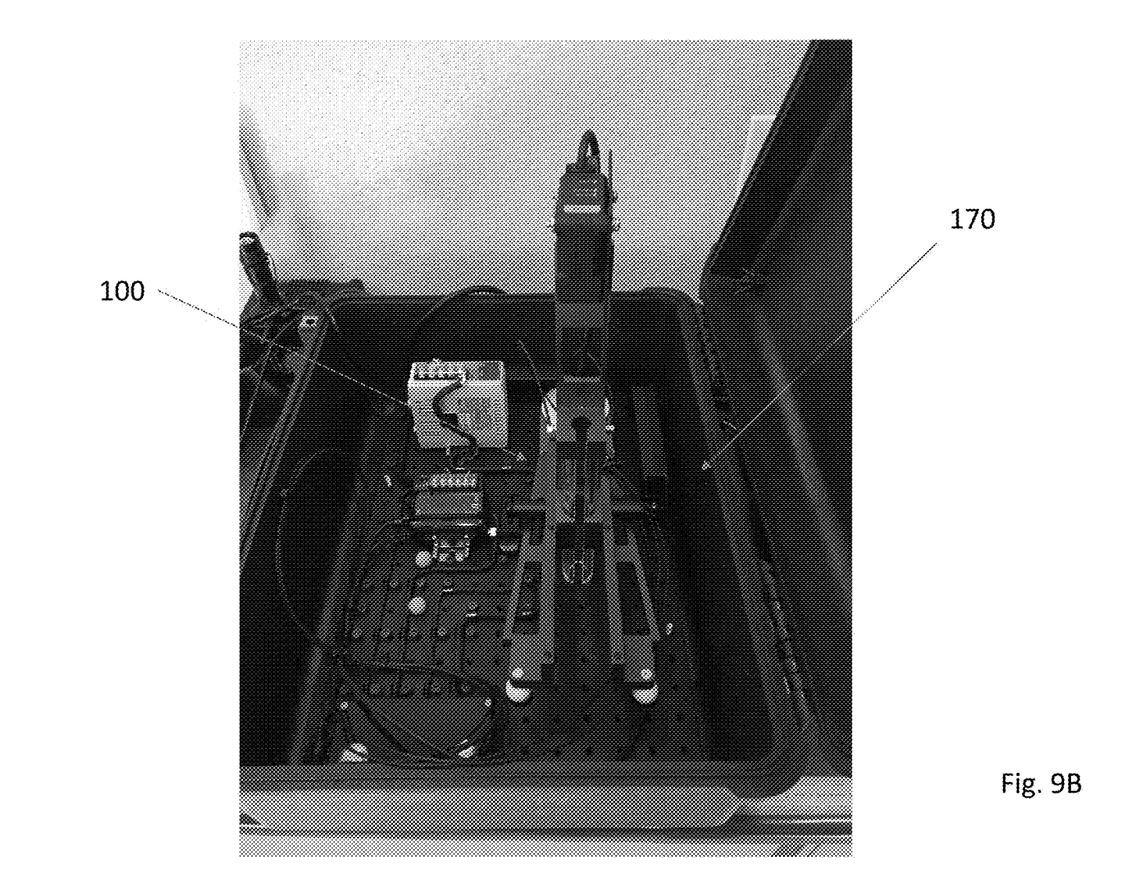

FIGS. 9A and 9B show a case 170 of the type which may be used to store the system 100 including the frame member 110, ball-drop tube 120, laser 130 and sensors 167, 168. In addition, the case 170 contains hardware/software configured to receive data (e.g., bounce height) captured by the laser 130 and/or sensors 167, 168. In one embodiment, a RS232 device transmits data from the operational system connected to the roulette wheel being tested to memory and software designed to evaluate the data. In one embodiment, a keyboard wedge program captures numeric values sent from the RS232 device automatically entering the data into a custom spread sheet. The hardware and software may be contained within the case creating a portable system capable of being transported to the roulette wheel rather than the roulette wheel having to be transported. The vertical unit 113 may be positioned generally parallel to the horizontal unit 111 for purposes of storage in the case.

Figure 10:
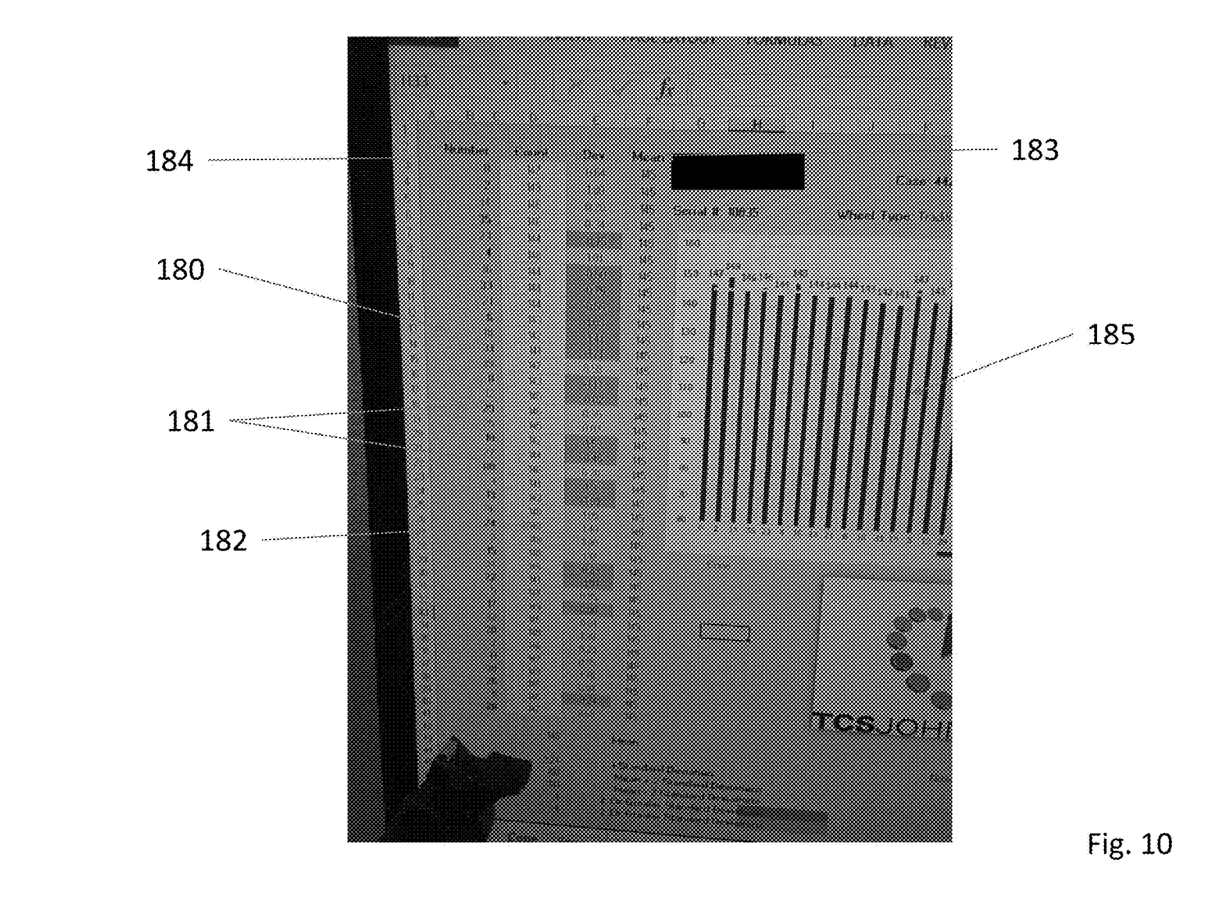
FIG. 10 illustrates a visual presentation of data captured by the system according to the embodiments of the present invention.

FIG. 10 shows an exemplary output 180 of the captured data. As shown, each of the 37, 38 or 39 ball pockets 181, depending on the wheel configuration, about number ring 155 has been tested resulting in a detected bounce height 182, and standard deviation 183 associated with the ball drops. A mean bounce height 184 is listed for comparison.

In one embodiment, a bounce height falling outside of 2 standard deviations from the mean, is flagged as a problem. The mean bounce height 184 may be pre-programmed based on the roulette wheel materials and properties, or may be generated in real time from captured data. A graphical representation 185 of the various bounce heights may be presented as well.

Figure 11:
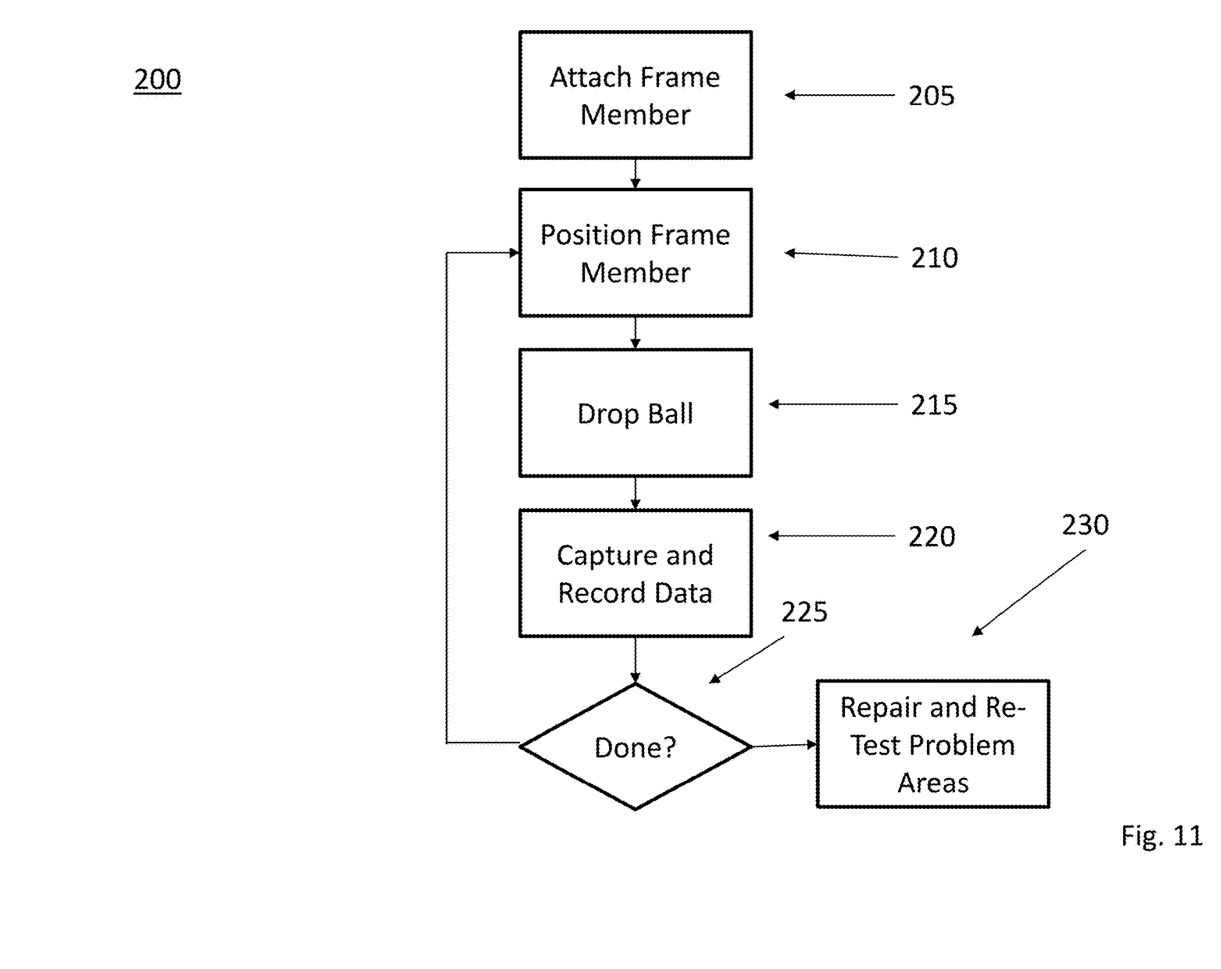
FIG. 11 illustrates a flow chart detailing one method of utilizing the system according to the embodiments of the present invention.

FIG. 11 shows a flow chart 200 detailing one method of utilizing the system 100 described herein. At 205, the frame member 110 is attached to the turret support 152 of the roulette wheel. At 210, the ball-drop tube 120 is positioned over the desired area of the roulette wheel. The ball-drop tube 120 may be slid along the spaced slots 161, 162 to the cone 153, the separator ring 154 including the ball pockets, the number ring 155 and the lower ball track 156, and rotated 360° around the roulette wheel. That is, the ball-drop tube 120 may be positioned over most of the wheel areas with which a properly spun roulette ball makes contact during game play. Once the ball-drop tube 120 is positioned, at 215, the roulette ball is dropped though the ball-drop tube. At 220, ball-drop data is captured and transmitted to memory and software tools for evaluation. The data may further be displayed. At 225, it is determined if all desired roulette wheel areas have been tested. If not, the chart 200 loops back to 210 for re-positioning. If all areas have been tested, at 230, any roulette wheel areas underperforming are repaired and re-tested by qualified personnel.

In an alternative embodiment, sound waves caused by the roulette ball dropping on the roulette wheel are measured using sound detection equipment. For example, oscilloscopes, microphones, sound level meters and/or recorders and the like can be used to detect sound waves generated by the roulette ball impacting the various parts of the roulette wheel as described above. Like the laser measurements detailed above, based on variances in the detected sound waves, dead spots and hot spots may be identified. That is, a higher amplitude sound wave is indicative of a louder sound wave and vice versa. If a sound wave amplitude is lower than a determined normal or mean amplitude, then it may be indicative of a dead spot and if a sound wave amplitude is higher than a normal or mean amplitude, then it may be indicative of a hot spot. For sound wave amplitudes that are, for example, 2 standard deviations from the mean sound wave amplitude may require roulette wheel repair to correct the defect.

Figure 12:
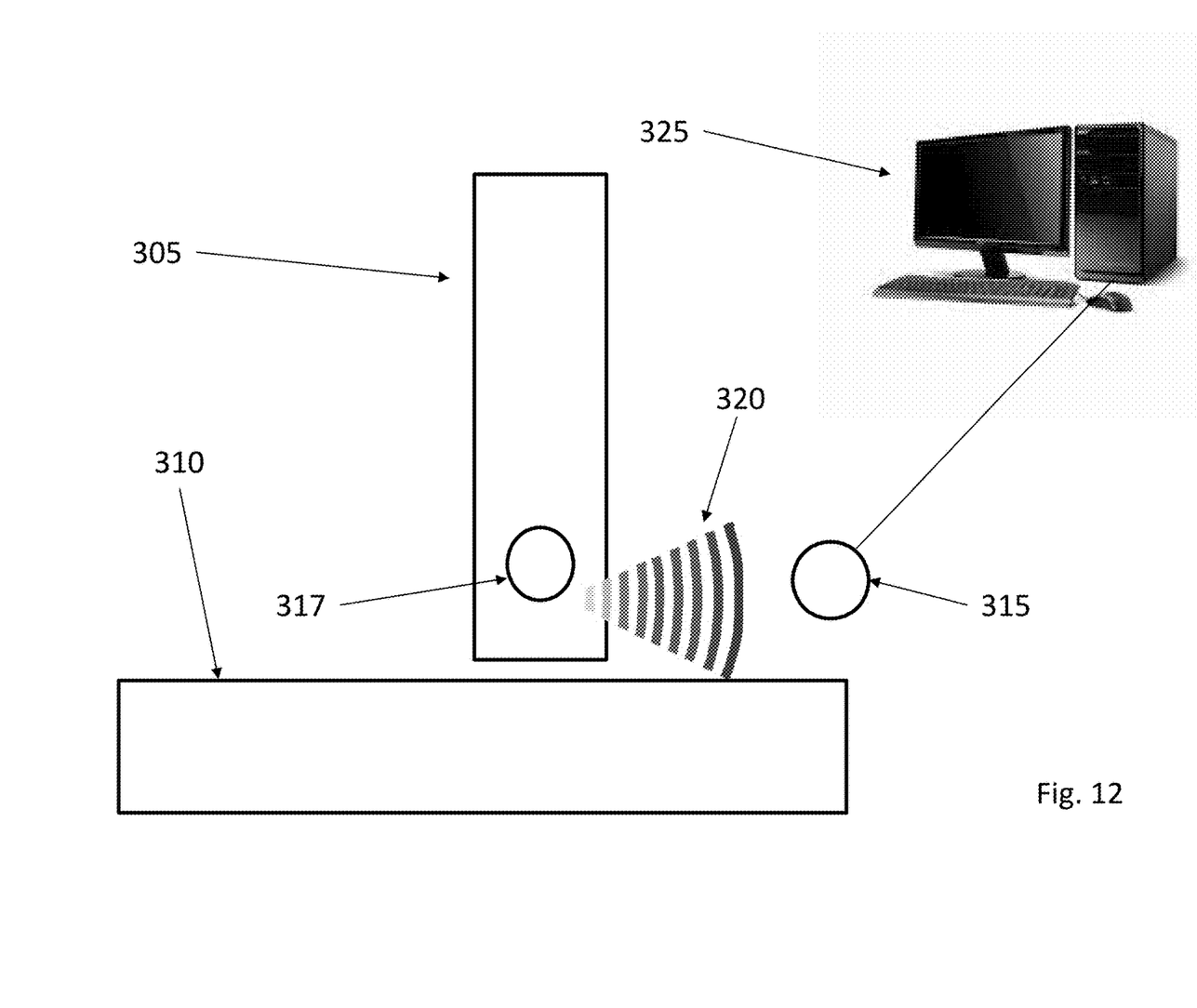
FIG. 12 illustrates an alternative embodiment using acoustic measurements according to the embodiments of the present invention.

FIG. 12 shows a block diagram of an acoustic system 300 according to the embodiments of the present invention. A ball-drop tube 305 is positioned above a roulette wheel 310 as detailed above. A sound-detection device 315, such as a microphone or sound level meter, is positioned near the point of contact between a roulette ball 317 dropped through the ball-drop tube 315 and the roulette wheel 310. The amplitudes of sound waves 320 created by said contact are captured by the sound-detection device 315 and transmitted to a computer system 325 for recordation and analysis. The sound-detection device 315 may also record the amplitude of the sound waves 320 before transmitting the same to the computer system 325. The analysis of the sound wave amplitudes is similar to the analysis of the ball height data. More particularly, the sound wave amplitudes for different roulette wheel regions are compared to one another to look for anomalies. For example, any sound wave amplitude falling 2 or more standard deviations from the mean sound wave amplitude may be indicative of a dead spot or hot spot.

Although the invention has been described in detail with reference to several embodiments, additional variations and modifications exist within the scope and spirit of the invention as described and defined in the following claims.

We claim:

1. A system comprising:
   a frame member rotatably attachable to a roulette wheel proximate a turret support;
   a ball-drop tube slidably engaged to said frame member, said ball-drop tube slidable from near a center of said roulette wheel to an outer section of said roulette wheel; and
   a laser positioned to measure at least a bounce height of a roulette ball dropped through said ball-drop tube onto one or more of the following: a cone, separator ring, number ring and lower ball track of said roulette wheel.

2. The system of claim 1 further comprising one or more sensors positioned to trigger said laser responsive to a roulette ball being dropped through said ball-drop tube.

3. The system of claim 1 further wherein said laser is affixed to a vertical member of said frame member.

4. The system of claim 1 wherein said ball-drop tube includes a cut-out along at least a portion thereof.

5. The system of claim 2 wherein said one or more sensors are positioned proximate to an upper opening of said ball-drop tube.

6. The system of claim 1 further comprising a hinged flanged, said hinged flange configured to permit said frame member to pivot upward.

7. A system comprising:
   a frame member rotatably attachable to a roulette wheel proximate a turret support;
   a ball-drop tube slidably engaged to said frame member, said ball-drop tube slidable from near a center of said roulette wheel to an outer section of said roulette wheel;
   a laser positioned to measure at least a bounce height of a roulette ball dropped through said ball-drop tube onto one or more of the following: a cone, separator ring, number ring and lower ball track of said roulette wheel;
   means for transmitting bounce height data to a software application configured to evaluate the same; and
   means for displaying said bounce height data.

8. The system of claim 7 further comprising one or more sensors positioned to trigger said laser responsive to a roulette ball being dropped through said ball-drop tube.

9. The system of claim 7 further wherein said laser is affixed to a vertical member of said frame member.

10. The system of claim 7 wherein said ball-drop tube includes a cut-out along at least a portion thereof.

11. The system of claim 8 wherein said one or more sensors are positioned proximate to an upper opening of said ball-drop tube.

12. The system of claim 7 further comprising a hinged flanged, said hinged flange configured to permit said frame member to pivot upward.

13. A method of identifying roulette wheel biases comprising:
   (i) rotatably attaching to a roulette wheel a device comprising a frame member, ball-drop tube connected to said frame member, and at least a laser configured to measure a roulette ball bounce height;
   (ii) positioning said frame member and ball-drop tube such that said ball-drop tube is above a cone, separator ring, number ring or lower ball track of said roulette wheel;
   (iii) dropping a roulette ball into said ball-drop tube for making contact with said cone, separator ring, number ring or lower ball track of said roulette wheel;

(iv) recording at least a bounce height of said roulette ball after making contact with said cone, separator ring, number ring or lower ball track of said roulette wheel in step (iii);
(v) repeating steps (ii)-(iv) as necessary; and
(v) evaluating said at least bounce heights associated with all ball drops to determine roulette wheel biases.

14. The method of claim 13 further comprising transmitting said at least bounce height data to a software application configured to evaluate the same.

15. The method of claim 13 further comprising transmitting said at least bounce height data to a display.

16. The method of claim 13 further comprising after step (iv), pivoting said frame member upward and collecting said roulette ball from beneath said ball-drop tube.

* * * * *